United States Patent [19]

Van Der Goes et al.

[11] Patent Number: 5,801,048
[45] Date of Patent: Sep. 1, 1998

[54] PROCESS FOR PRODUCING 7B-(4-CARBOXYBUTANAMIDO)-CEPHALOSPORANIC ACID ACYLASE ("GA") ENZYME

[75] Inventors: Wilhelmus Van Der Goes, Turin; Antonella Bernardi, Novara; Aldo Bosetti, Vercelli; Giuliana Franzosi, Calvignasco; Pietro Cesti, S. Martino Di Trecate, all of Italy

[73] Assignee: Ministero Dell 'Universita' E Della Ricerca Scientifica E Tecnologica, Rome, Italy

[21] Appl. No.: 712,389

[22] Filed: Sep. 11, 1996

Related U.S. Application Data

[63] Continuation of Ser. No. 366,457, Dec. 30, 1994, Pat. No. 5,612,210.

[30] Foreign Application Priority Data

Jan. 14, 1994 [IT] Italy ........................ MI.94A/000031 U

[51] Int. Cl.$^6$ .............. C12N 1/21; C12N 15/70
[52] U.S. Cl. ................ 435/252.33; 435/252.3; 435/320.1
[58] Field of Search ............ 435/252.33, 252.3, 435/320.1, 254.1; 536/23.2

[56] References Cited

FOREIGN PATENT DOCUMENTS 0 504 798  3/1992  European Pat. Off. .

OTHER PUBLICATIONS

Matsuda et al. "Cloning and characterization of the genes for two distinct cephalosporin acylases from a Pseudomonas strain" J. Bacteriology 169 (12): 5815–5812, Dec. 1987.

Brosius et al. "Regulation of ribosomal RNA promoters with a synthetic lac operator." Proc. Nat. Acad. Sci., USA 81: 6929–6933, Nov. 1984.

Matsuda et al. "Molecular cloning and structure of the gene for 7β-(4-carboxybutanamido)cephalosporanic acid acylase from a Pseudomonas strain". J. Bacteriology 163 (3): 1222–1228, Jul. 1985.

*Primary Examiner*—Robert A. Wax
*Assistant Examiner*—Gabriele E. Bugaisky
*Attorney, Agent, or Firm*—Oblon, Spivak, McClelland, Maier & Neustadt, P.C.

[57] ABSTRACT

The present invention relates to a process for producing large amounts of 7β-(4-carboxybutanamido)-cephalosporanic acid acylase ("GA") enzyme, which process consists in growing, under suitable culture conditions, a recombinant *Escherichia coli* K12 strain and subsequently extracting the enzyme from the resulting culture.

Enzyme production is controlled by a particular expression system which can be induced by corn-steep liquor, an extremely low cost component of the culture medium.

The enzyme can be used in the enzymatic preparation of 7-amino-cephalosporanic acid by starting from 7β-(4-carboxybutanamido)-cephalosporanic acid.

6 Claims, 4 Drawing Sheets

PROCESS FOR PRODUCING 7B-(4-CARBOXYBUTANAMIDO)-CEPHALOSPORANIC ACID ACYLASE ("GA") ENZYME

This is a continuation of Application No. 08/366,457, filed Dec. 30, 1994, which matured into U.S. Pat. No. 5,612,210. This continuation is entitled to the benefit of priority based on priority papers filed in the parent Application No. 08/366,457.

BACKGROUND OF THE INVENTION

1. Field of the Invention

The present invention relates to a process for producing large amounts of 7-(4-carboxybutanamido)-cephalosporanic acid acylase ("GA") enzyme, which process consists in growing, under suitable culture conditions, a recombinant *Escherichia coli* K12 strain and subsequently extracting the enzyme from the resulting culture.

2. Description of the Background

Enzyme production is controlled by a particular expression system which can be induced by Corn Steep Liquor, an extremely cheap component of the culture medium. Furthermore, in particular an *E. coli* K12 derivative is used, which is regarded as "safe" by EEC regulations.

The enzyme can be used in the enzymatic preparation of 7-amino-cephalosporanic acid starting from 7-(4-carboxybutanamido)-cephalosporanic acid.

In particular, accomplishing the invention implied:

- isolating a gene coding for 7-(4-carboxybutanamido)-cephalosporanic acylase enzyme from *Pseudomonas* sp. 146H9 (NCIMB40474) and SY77-1 (Ferm2410), by means of recombinant DNA techniques;
- cloning said gene into an *Escherichia coli* K12 microorganism classified as a "safe" one (class P1);
- producing large amounts of enzyme by fermentation of said *E. coli* strain;
- extracting and immobilizing the enzyme for the enzymatic preparation of 7-aminocephalosporanic acid from 7-(4-carboxybutanamido)-cephalosporanic acid.

In nature, several microorganisms exist which are capable of producing 7-(4-carboxybutanamido)-cephalosporanic acid acylase (GA) enzyme. It was observed that such a capability is diffused, in particular, in *Pseudomonas* spp. [Shibuya Y. et al (1981) Agr. Biol. Chem. 45, 1561; Matsuda A. et al (1985) J. Bacteriol. 163, 1222; Matsuda A. et al (1987) J. Bacteriol. 169, 5815; Aramori I. et al J. Ferm. & Bioeng. 72, 227 (1991)].

However, the implementation of a whatever industrial process for GA enzyme production is hindered by the low productivity levels of above said microorganisms (3–4 U/l).

A route which was successfully tried to obtain meaningful increases in production of GA enzyme, consists in using recombinant DNA techniques. In practice, this technology enables the GA enzyme coding gene to be isolated from a producer microorganism, and to be transferred into an *E. coli* strain in which its expression is put under regulation by a strong promoter.

By means of such a technology, Croux et al. (EP 0 469 919 A2) modified an *E. coli* K12 strain and, after growing it on a suitable culture medium, they obtained a meaningful yield increase, reaching enzyme production levels of 3000 U/l. Unfortunately, the microorganism they used is a wild type with no repressors and therefore enzyme production cannot be regulated and controlled by using inducers. Owing to the above reasons, EEC regulations assign Croux et al. microorganism to Class P3 for which considerable limitations are contemplated.

Another example of improvement in the production capabilities of microorganisms accomplished by recombinant DNA techniques is reported in EP 0 504 798 A1 (10,000 U/l).

In this case, an *E. coli* K12 derivative is used which is classified as a "safe" microorganism belonging to Class P2, therefore not subject to such limitations as mentioned above. Said *E. coli* derivative contains repressors which prevent enzymatic activities from being produced unless a suitable inducer is present. However, the only example of an inducer reported in technical literature is IPTG (isopropyl BD-thiogalactopyranoside), a highly expensive substance.

SUMMARY OF THE INVENTION

The present Applicant surprisingly succeeded now in locating a GA gene expression system which can be induced by such an extremely cheap substance as Corn Steep Liquor, which also is a component of the culture medium.

Said system allows large amounts of enzyme to be produced even when, as the host organism harbouring the expression system, a particular derivative of *E. coli* K12 is used, which is classified as a very safe one (Class P1) by EEC regulations.

Therefore, present Applicant's invention relates to a process for producing large amounts of 7-(4-carboxybutanamido)-cephalosporanic acid acylase ("GA") enzyme, which process comprises growing and inducing, on a suitable culture medium, an *E. coli* strain containing the acylase coding sequence and subsequently extracting the enzyme from the resulting culture, characterized in that as the inducer Corn Steep Liquor is used, and as the producer microorganism an *E. coli* strain is used which is selected from NCIMB40560, NCIMB840559, NCIMB40592 and NCIMB40593.

Obtaining the high-producer *E. coli* derivative implied developing a process which comprises the following steps:

(a) digesting total DNA of a microorganism containing the sequence coding for GA enzyme and producing a bacteriophage DNA library;

(b) infecting *E. coli* with the phages of the library;

(c) identifying host *E. coli* clones containing a portion of acylase sequence by using a purified antiserum specifically directed against the acylase of interest;

(d) screening *E. coli* clones containing the complete acylase sequence by hybridization with a probe containing a partial sequence of acylase gene and determination of the enzymatic activity thereof;

(e) isolating the plasmid, characterizing the necessary DNA region for GA synthesis and inserting it into a high-level expression vector of *E. coli*;

(f) modifying the high-level expression vector in order to hinder β-lactamase production from host strain plasmid;

(g) optimizing the growth of expression plasmid containing *E. coli* by batch fermentations and fed-batch fermentations, using different carbon and nitrogen sources.

DETAILED DESCRIPTION OF THE INVENTION

Figure 1:
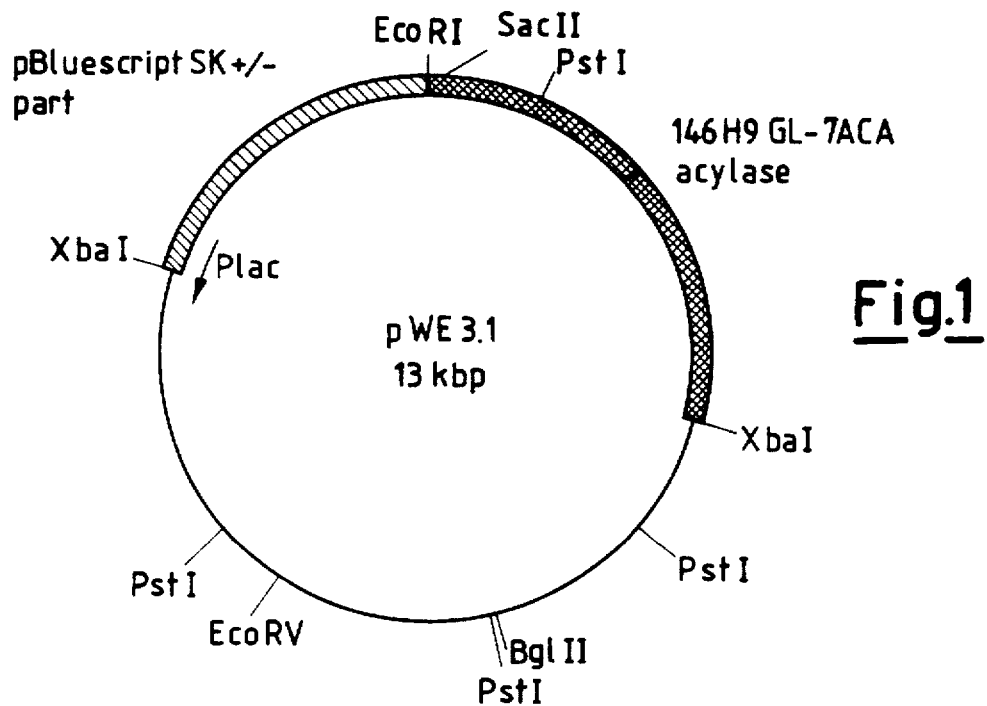
FIG. 1 is s plasmid map of pWE3.1.

As DNA donors, *Pseudomonas* strains 146H9 (NCIMB40474) and SY77-1 (Ferm2410) were used. These are capable of producing only small amounts of GA enzyme (3U/l and 4U/l, respectively).

Chromosomal DNA was extracted, purified and partially digested with restriction enzymes. The so obtained DNA fragments were treated at their terminal ends and were then inserted into a bacteriophage lambdaZAPII vector (Stratagene). Recombinant phages were plated with *E. coli* cells in order to generate a *Pseudomonas* 146H9 (NCIMB40474) and SY77-1 (Ferm2410) bacteriophage lambda lambdaZAPII gene library.

In order to perform the screening of the libraries generated from genomic DNA from *Pseudomonas* strains, antibodies were prepared which are capable of recognizing GA enzyme, according to the following procedure:

GA enzyme produced by *Pseudomonas* strain 146H9 was first purified and then was injected to rabbits. Then GA-specific antiserum was obtained, the sensitivity of which was proved to be optimal for library screening (this antiserum, after being diluted 200–1000× is still capable of specifically recognizing 10–100 Pg of GA enzyme spotted on a nitrocellulose paper filter). The positive reaction between the antibody and the enzyme was not altered by the addition of *E. coli* cellular lysate to the sample being tested. The antiserum directed against GA from *Pseudomonas* 146H9 strain (NCIMB40474) is also capable of recognizing purified GA from *Pseudomonas* strain SY77-1 (Ferm2410).

In that way, partial sequences of GA DNA were isolated.

Said sequences, after being labelled and used as probes to probe said gene libraries, allowed complete GA sequences to be isolated.

A further confirmation of the presence of acylase genes in the libraries generated with the DNA from *Pseudomonas* strain 146H9 (NCIMB40474) and SY77-1 (Ferm 2410) was obtained by operating according to two different procedures:

(1) Measurement of acylase activity of transformed colonies by HPLC or colorimetric technique [Matsuda A. et al (1985) J. Bacteriol. 163, 1222; Matsuda A. et al (1987) J. Bacteriol. 169; Aramori I. et al J. Ferm. & Bioeng. 72, 232 (1991)].

(2) Hybridization with oligonucleotide probes homologous to already known sequences of acylase gene and therefore capable of recognizing plasmids containing the genes of interest (EP 0 504 798 A1). Those cells of *E. coli* which harboured the plasmids with the identified sequences displayed acylase activity.

Those DNA fragments which contained GA gene were furthermore restricted by removing any adjacent non-enzyme-coding DNA.

The resulting fragments were then cloned into an expression vector of *E. coli* and were then put under the regulation by a strong inducible promoter.

Promoter induction made it possible an acylasic activity, both volumetric and specific, to be obtained which was much higher than of donor *Pseudomonas* 146H9 (NCIMB40474) and SY77-1 (Ferm2410) strains.

In order to isolate the GA gene in E. coli, vectors lambdaZAP II and pBluescript SK+/-(Stratagene) were used.

In order to express the fusion protein β-galactosidase-GA in a gene library, both of bacteriophage and of colonies with plasmids, as well as also such vectors as lambdagt11, lambdagt22 or plasmids, as the pUC series, or still other vectors having expression modules for fusion proteins, can anyway be used.

In detail, acylase genes were cloned, as follows.

Chromosomal DNA from donor strains was partially digested with a frequent-cleavage restriction enzyme and the resulting fragments were selected according to their length; the fragments falling within a desired length range were treated with DNA modifying enzymes such as, e.g., nuclease (Bal31), in order to generate casual terminal ends, and DNA polimerase (Klenow fragment), in order to fill said terminal ends. Thereafter, linkers were attached to these fragments, which consist of phosphorylated oligonucleotides by means of T4 DNA ligase. So treated fragments were then cleaved with a restriction enzyme (which cleaves the linker sequence) and were then separated from non-bound linkers by gel filtration. The DNA vector (a bacteriophage in the case of a phage gene library or a plasmid in the case of a plasmid gene library) was also digested with a restriction enzyme which generates, on DNA terminal ends, complementary sequences to those present on terminal ends of modified donor DNA. Both the vector and the so obtained fragments were then ligated by means of T4 DNA ligase. The recombinant vectors, resulting from the insertions of one or more DNA fragments from donor microorganism into the vectors, can be used in order to transform a suitable microorganism, as *E. coli* XL1-Blue, by means of an infective route (phage gene library) or using conventional transformation techniques as described in Maniatis, T. et al (1989) Molecular Cloning: A Laboratory Manual, Cold Spring Harbor Laboratory, Cold Spring Harbor, N.Y., U.S.A. (plasmid gene library).

The gene library is plated and induced to express the fusion proteins. On the plates nitrocellulose membranes are subsequently applied in order to bind the produced proteins. The membranes are then assayed by an immune test, by exposing them to the specific antiserum for GA (at a suitable dilution), revealing which plaque or colony contains a partial GA sequence. Once the vector of interest is located, a restriction map of the insert is prepared.

Still using the above disclosed gene library, its DNA is analyzed after transferring it to a nitrocellulose membrane by the "plaque or colony lifting" technique [Maniatis, T. et al (1989)].

Then, the DNA-DNA hybridization is used: the labelled probe (by conventional techniques, using the "Boehringer Non-Radioactive Labelling Kit"), constituted by a fragment close to the β-galactosidasic portion of the fusion protein, is capable of evidentiating the presence of the gene corresponding to GA enzyme in the gene library. Under suitable conditions of DNA-DNA hybridization, the GA specific probe only anneals to the recombinant vectors which contain either a portion or full-length coding gene.

The so located plaques or colonies were then tested for their capability of producing GA and a restriction map of the insert was prepared. The DNA fragment was then restricted to the minimum length necessary for acylasic activity synthesis and was then transferred to the *E. coli* host cell. Once the restriction map of the insert is defined, deletions can be carried out on DNA fragment using restriction enzymes or DNA nucleases, in order to define the GA gene position with higher precision.

The restriction map was determined by using several restriction enzymes, and the acylasic activity was quantified by means of conventional spectrophotometric or HPLC techniques.

The GA expression level in *E. coli* was enhanced by means of already known conventional genetic engineering techniques. According to one of these, the interesting gene is put under the control by *E. coli* promoter sequences, as $P_{lacUV5}$, $P_{tac}$, $P_{trc}$, $P_{trp}$, $P_{phoA}$, $P_{lpp}$, $P_L$, $P_R$, Plambda$_{10}$, or other promoters used for gene expression in *E. coli*.

In our case, the recombinant vector containing the GA gene was digested with several restriction enzymes. The resulting DNA fragments were bound, using T4 DNA ligase, to plasmids as pBR3Z2, pBluescript, pUC18, pACYC184, or still other plasmids previously digested with restriction enzymes displaying compatible sites with the fragments they should contain. The resulting recombinant vectors were then introduced, by transformation, into an *E. coli* strain, as XL1 Blue. Those transformants which produce GA can be recognized by measuring the acylasic activity of their cellular extracts. The position of GA gene on the DNA fragment was determined by means of the restriction map of the recombinant vector. The gene containing fragment is suitably restricted and is then inserted into a plasmid containing a $P_{tac}$ promoter sequence [de Boer, H. et al (1983) Proc. Natl. Acad. Sci. USA80:21], e.g., pKK223-3 or pDR540, or a $P_{trc}$ promoter sequence, as pKK233-2 and pTrc99A (Pharmacia). A recombinant vector containing the GA gene under the control of $P_{tac}$ promoter was used in order to transform *E. coli* XL1 Blue cells, and GA activity of transformants was assayed as disclosed above.

In this way, strains of *E. coli* were obtained which are capable of producing much more GA than strains of *E. coli* containing the only GA genes derived from *Pseudomonas* 146H9 (NCIMB40474) and SY77-1 (Ferm2410) can do. The high production yield obtained in this step, derives from the use of specific promoter sequences for *E. coli* which determine a high level expression of the gene. In fact, the GA gene has a promoter of its own which operates well in *Pseudomonas*, but not in *E. coli* so when it is harboured in this host, said gene displays a low expression level. Changing the promoter causes a substantial improvement of the process of the instant patent.

The *E. coli* strains used for the high expression level of the GA genes of *Pseudomonas* 146H9 (NCIMB40474) and SY 77-1 (Ferm2410) can be, e.g., XL1 Blue, JM105, W3110, DH1, and so forth.

The gene for ampicilline resistance contained in pKK223-3 vector (responsible for the production of β-lactamase from plasmid origin) can be replaced by the genes coding for tetracycline, chloramphenicol, kanamycin, streptomycin resistance, or still other known genes for resistance to antibiotics.

The production of GA is carried out by growing the recombinant *E. coli* strains inside shaked Erlenmeyer flasks or fermentors containing a suitable culture medium.

The fermentation time may be comprised within 12–90 hours.

The culture medium is composed by a carbon source such as, e.g., glucose, lactose, sucrose, glycerol, fructose, molasses, vegetable oils, and so forth; a source of nitrogen/vitamins such as, e.g., yeast extract, meat extract, soybean meal, peanut meal, Corn Steep Liquor, and so forth, and mineral salts.

The growth temperature is 18°–37° C., and the pH value of the broth is 5–9.

The stability of the plasmids during the fermentations which require a certain number of generations can be maintained by means of the addition of antibiotics.

It was observed that GA production can be improved by the "fed-batch" technique.

Such a technique consists in growing the recombinant *E. coli* strain in a Corn Steep Liquor based medium until an equilibrium stage is reached to which a slow growth corresponds, and then reaching a plentiful growth by adding a carbon source, as glucose or glycerol.

The production of GA with those *E. coli* strains with LacI$^q$ genotype, as JM105 or XL1 Blue, or with LacI$^q$ present on the same expression plasmid, is induced by means of the addition of expensive substances to the fermentation broth such as, e.g., IPTG (isopropyl β D-thiogalactopyranoside; EPO 504 798 A1). IPTG causes the derepression of *E. coli* promoters derived from the Lac gene ($P_{lacUV5}$, $P_{tac}$, $P_{trc}$).

This necessary and expensive induction can be avoided if Corn Steep Liquor is used in the fermentation broth at a concentration of 1–20% volume/volume (v/v).

Therefore, a surprising result of the present invention consists in the possibility of inducing the GA gene, under control of $P_{tac}$ promoter, in a *E. coli* LacI$^q$ strain, by using a low-cost medium component.

Furthermore, the presence of Corn Steep Liquor preserves the plasmid stability and the expression of GA enzyme during the fermentation.

Corn Steep acts as an inducer also when the high-expression plasmid containing the *E. coli* promoter deriving from Lac gene (e.g. $P_{lacUV5}$, $P_{tac}$, $P_{trc}$) is contained inside cells of *E. coli* strains with Lac genotype, as W3110, (ATCC27325) or DH1.

However, in these cases, problems of plasmid stability and, consequently, of GA gene expression, were observed.

The production of GA enzyme by means of a fermentation process implying the use of a recombinant microorganism is liable to EEC regulation.

These classify the host microorganism according to three parameters: damage factor, expression factor, and access factor.

The damage factor takes into consideration the nature of the product obtained from the recombinant microorganism: e.g., GA is attributed a value of $10^9$, because this enzyme is constituted by a chemically active molecule which does not cause damages to living beings.

The expression factor is 1 when the expression for recombinant GA production is maximal.

Finally, the access factor depends on the *E. coli* strain and on the plasmid type used.

The wild type strains of *E. coli* which display the capability of developing inside human colon, are attributed an access factor of 1; those *E. coli* strains which are derived from K12 strain (for example, W3110), which do not bear debilitant mutations, are attributed an excess factor of $10^{-3}$; and, finally, such strains as *E. coli* K12-derived but debilitated as XL1 Blue, JM105, DHI, and so forth, are classified with an access factor of $10^{-6}$.

The product of these three factors is used in order to classify the genetically modified microorganism in the so-said "containment categories". In our case, the production of GA by using a high-expression plasmid in the three types of *E. coli* as mentioned above, is of $10^{-9}$, $10^{-12}$, $10^{-15}$, respectively, to which "containment categories" correspond which are of 0, 1 and 2, respectively ("zero" means that no restrictions are necessary for using these microorganisms in fermentation processes on full industrial scale; vice-versa, a value of "2" means that stringent restrictions have to be adopted).

The GA produced by the recombinant microorganism can be recovered after separating the cells from the culture broth by centrifugation.

The cells are then broken using conventional methods as sonication, osmotic shock, pressure, enzymatic lysis (lysozime), and so forth, and GA enzyme is purified by the cellular extract by precipitation, chromatographic techniques and use of membranes.

It was found that, by means of a simple ammonium sulfate gradient (30–55%) and a weak anionic exchange chromatography (DEAE-SEPHACEL (2-(Diethylamino)ethyl cellulose, Pharmacia), such enzymes as esterases or β-lactamases (which can destroy or modify the substrate and the product of the reaction catalyzed by GA) can be completely removed from those fractions which contain GA.

The resulting advantage is that the enzyme is obtained at a high enough purity level to be capable of being immobilized, with no need for using *E. coli* strains which are incapable of producing esterases or β-lactamases, or for replacing their ampicillin resistance with resistance to other antibiotics.

The partially purified and concentrated enzymatic extracts can be immobilized by causing them to react with suitable inert supports (such as, e.g., Eupergit C).

The immobilized enzyme is cyclically used for transforming solutions of GL-7ACA and isolating 7ACA according to well-known techniques.

The following examples are presented in order to illustrate the process of the present invention in greater detail and should not be understood as being limitative of the purview of the same invention, as it is defined in the appended claims.

EXAMPLE 1

Antibody preparation

The GA enzyme from cells of *Pseudomonas* 146H9 (NCIMB40474) was purified by means of conventional methods, until homogeneousness. Antibody preparation and testing is a conventional immunological technique. All purification operations were carried out under 5° C. if not differently specified. GA activity was measured according to the Balasingham method modified for 7ACA instead of 6APA (Balasingham, K. et al Biochim. Biophys. Acta (1972), 276:250); 1U is the enzyme amount which is needed to produce 1 μmol of 7-amino-cephalosporanic acid during 1 minute at 37° C. and at an optimal pH value of 7–11.

EXAMPLE 2

1. Purification of GA enzyme derived from *Pseudomonas* sp 146H9 (NCIMB40474)

a. The cells are collected from the fermentation broth by continuous centrifugation at 12000 g. The cell pellets are stored at −20° C.; 100 g of frozen cellular pellet is suspended in 300 ml of start buffer (5 mM Tris.Cl, 0.1M NaCl pH8.0) and this suspension is sonicated (six treatments of 5 minutes each at 200 W, with cooling between treatment) until complete breakage of cells is reached. Non-lysed pellet and "debris" are removed by centrifugation at 25000 g during 45 minutes.

b. 30–55% ammonium sulfate gradient. Solid ammonium sulfate is added to cell-free extract, c.f.e., kept with stirring by means of a magnetic stirrer and at 0° C. The pH value is kept at 8.0 with $NH_4OH$. The precipitate formed within one hour of the addition of the salt fraction which determines a 30% saturated solution is centrifuged at 4000 g during 45 minutes at 0° C. Then, further portions of solid ammonium sulfate are added to the supernatant, as disclosed above, until a 55% saturated solution is obtained. After one hour stirring at 0° C. the precipitate is collected by centrifugation (see above), is dissolved in fresh start buffer and dialyzed against the same buffer.

c. Chromatography on DEAE-SEPHACEL Column. The dialysate containing the GA enzyme obtained as disclosed in above b. step, was applied to a DEAE-SEPHACEL column [500×32 mm I.D. 200 ml volume] previously equilibrated with start buffer. After column washing with 100 ml start buffer, the GA enzyme was eluted with a linear NaCl gradient (0.1->35M, 400ml in each container) in 50 mM Tris.Cl pH 8.0; the flow rate through the column was 40 ml/hour throughout the purification steps; fractions of 20 ml were collected. The GA containing fractions were then pooled, concentrated by ultrafiltration down to 100 ml and dyalized against 50 mM Tris.Cl 0.1M NaCl pH 8.8 (Q-start buffer).

d. Chromatography on Q-SEPHAROSE fast flow column. The dialysate containing the GA enzyme obtained from above c. step was applied to a Q-SEPHROSE fast flow column [500×32 mm I.D., V=200 ml] previously equilibrated with Q-start buffer. After column washing with 100 ml Q-start buffer, GA enzyme was eluted with a linear NaCl gradient (0.1→0.35M, 400 ml in each container) in 50 mM Tris.Cl pH 8.8; during all purification steps, the flow rate through the column was 20 ml/hour, with fractions of 10 ml each being collected. The GA containing fractions were then pooled, concentrated by ultrafiltration to an end volume of 15 ml and dialyzed against 10 mM sodium phosphate pH 7, 30% saturated ammonium sulfate (HIC start buffer).

e. Chromatography on Octyl-SEPHAROSE CL4B column. The solution of GA enzyme obtained from the previous step was applied to an Octyl-SEPHAROSE CL4B column [500×16 mm (I.D.); V=30 ml], previously equilibrated with HIC start buffer. After column washing with 30 ml HIC start buffer, the GA enzyme was simultaneously eluted with linear gradient with saturated ammonium sulfate (30%→0%) and ethylene glycol (0→40%), 250 ml in each container in 10 mM sodium phosphate pH 7.0; throughout the purification steps, the flow rate through the column was 10 ml/hour and 10 ml fractions were collected. Those fractions which contain GA were pooled and concentrated to 4 ml by ultrafiltration.

f. Gel filtration with Sephacryl S200HR. The solution of GA enzyme obtained from the e. step was applied to and eluted from a Sephacryl S200HR column (100×16 mm I.D., V=160 ml ) which had previously been equilibrated with 50 mM Tris.Cl 0.2M NaCl pH 8.0; throughout the purifications steps, the column was kept at a flow rate of 4 ml/hour and fractions of 2 ml were collected. Those fractions which contain GA enzyme were stored.

TABLE 1

Purification of GA from Pseudomonas 146H9 using an ammonium sulfate gradient, Ion exchange chromatography, hydrophobic Interaction chromatography and gel filtration

| Step/fraction | Pooled fractions (ml) | Total proteins (mg) | GA activity (U) | Yield (%) | Specific activity (U/mg) |
|---|---|---|---|---|---|
| a/c.f.e | 300 | 6500 | 65 | 100 | 0.01 |
| b/30–55% ammonium sulfate gradient | 110 | 2500 | 52 | 80 | 0.02 |
| c/DEAE-Sephacel | 120 | 656 | 49 | 75 | 0.07 |
| d/Q-Sepharose f.f. | 100 | 208 | 45 | 69 | 0.22 |
| e/Octyl-Sepharose CL4B | 150 | 2.6 | 37 | 57 | 1.63 |
| f/Sephacryl S200HR | 14 | 14.5 | 28.3 | 44 | 1.95 | g. Non denaturing PAGE. The fraction of gel filtration peak was further purified by non-denaturing polyacrylamide gel electrophoresis (PAGE). After staining of a gel segment, a major band and four minor bands were observed. The stained segment was then alligned with residual gel and the corresponding non-stained portion was cut. The GA enzymatic activity contained in so isolated gel was then evaluated, thus demonstrating that it is only contained in the gel segment corresponding to the major protein band. The acylase was then electroeluted from the gel placed inside a dialysis membrane (with 12 kD cut), and then in 37.6 mM Tris.Cl 40 mM Glycine pH 8.48 buffer, during 6 hours at 100 Volts and 5° C. The buffer was then discarded, except for the last 200 ml, which were used in order to resuspend any GA present on the membrane; the resulting suspension was submitted to denaturing PAGE.

h. Denaturing PAGE. Acylase recovered by electroelution was submitted to denaturation [5 minutes boiling in 0.1% sodium dodecylsulfate (SDS) and β-mercaptoethanol] and electrophoresis on 0.1% SDS PAGE gel with a known molecular weight standard. The staining with Coomassie Brilliant Blue or Silver staining showed two bands with molecular weights of 18 kD and 50 kD, respectively; these respectively correspond to the α-subunit and to the β-subunit of the enzyme. Some fractions of the gel filtration peak, submitted to SDS-denaturing PAGE and subsequently electroeluted, made it possible some milligrams of pure denatured GA enzyme to be obtained.

i. The pure denatured GA from the above h. step was mixed with complete Freund's adjuvant (Sigma) and the resulting mixture was injected to male white New Zealand rabbits, three times, each time at a dosage of 2 mg/injection, in order to raise antibodies. Thereafter, blood samples were collected, from which serum was separated. The latter was treated at 56° C. during 30 minutes and was then precipitated with 35%-saturated ammonium sulfate. The precipitate was purified with protein-Sepharose CL-4B (Pharmacia), to obtain the antibodies. The Dot blot testing confirmed that GA enzymes from Pseudomonas 146H9 (NCIMB40474) and SY77-1 (Ferm2410) strains and the purified antiserum as disclosed above react with each other yielding an immunoprecipitate. The IgG (immunoglobulin G) fraction obtained from a control rabbit, to which GA had not been injected, did not display immunoprecipitation with the GA enzymes.

2. Construction of a gene library with the DNA of Pseudomonas 146H9 (NCIMB40474) and SY77-1 (Ferm2410) strains.

Gene Libraries were constructed with the DNA from Pseudomonas 146H9 (NCIMB40474) and SY77-1 (Ferm2410) strains in lambdaZAPII, by means of the conventional techniques of recombinant DNA, as described in Maniatis, T. et al [Molecular Cloning: A Laboratory Manual, Cold Spring Harbor Laboratory, Cold Spring Harbor, N.Y., U.S.A. (1989)]. The enzymes were used following the instructions supplied by their respective suppliers. Genomic DNA was extracted from Pseudomonas sp. 146H9 and SY77-1 by using the method described in Silvahy T. et al [Experiments with Gene Fusions, Cold Spring Harbor Laboratory, Cold Spring Harbor, N.Y., U.S.A. (1984)]. The genomic DNA (25 µg) was partially digested with Sau3AI (2U) at 37° C. during 1 hour and the digestion mixture was submitted to electrophoresis on agarose gel (0.4%, 16 hours, 15 V), in order to obtain a purified DNA fraction with an average size of 4–10 kb. The DNA having the desired size was modified with Bal3I nuclease (10 U, 37 C, 30 min.); the reaction was quenched by extraction with phenol/chloroform and precipitation with ethanol. The terminal ends of the resulting casual DNA fragments were filled with Klenow DNA polymerase (10 U), dNTP's in nick-translation buffer (1 hour, 22° C.) and were then ligated with T4 DNA ligase (overnight, at 16° C.), to 5 µg of phosphorylated EcoRI-linkers and were then digested with 200 U EcoRI (4 hours, 37° C.). The DNA was separated from the excess of EcoRI linkers by chromatography on Sepharose CL4B column (Sigma), in order to obtain EcoRI fragments with a consistant average size, approximately of 5kbp. 0.1 µg of this DNA was ligated to 1µg of ZAPII bacteriophage, previously cut with EcoRI and dephosphorylated (Stratagene), by T4 DNA ligase (total reaction volume 5 µl), at room temperature during 1 hour and at 4° C. overnight.

The resulting mixture was submitted to "in vitro packaging", using "Gigapack Gold packaging extracts" (Stratagene). Plaque formation using E. coli XL1 Blue as the host organism, gave rise to about 100000 plaques. In the presence of X-gal and IPTG, approximately 95% of white plaques, with the residual being blue plaques, were observed. In that way, a gene library of genomic DNA constituted by about 100000 clones was produced.

A mixture of E. coli XL I-Blue culture (0.2 ml), the gene library lambdaZAPII: Pseudomonas 146H9 or SY77-1 (approximately 30000 clones) disclosed above and 7 ml of top agar were poured on a plate of LB agar (140 mm), which was then incubated at 42° C. for 4 hours. A nitrocellulose membrane (134 mm of diameter; Millipore) which had been previously kept immersed for 1 hour in a 10 mM IPTG solution and had subsequently been dried at room temperature, still for 1 hour, was then applied to the plate. The resulting assembly was incubated for 3.5 hours at 37° C. in order to allow genes to be expressed and their products to be transferred to the membrane. This technique, which is regarded as a very effective one, requires however a correct preparation of gene library DNA fragments: the beginning of any *Pseudomonas* genes which are inserted, must be in such a way as to enable the 39 $NH_2$-terminal aminoacids of β-galactosidase of lacZ' gene to be in reading frame relatively to it (this is the reason why the terminal ends of DNA of 146H9 and SY77-1 were modified).

From the approximately 30000 plaques tested by the blotting test, using a picoBlue immunodetection kit (Stratagene) and the antiserum specifically directed against GA, one positive plaque was located. The assay was carried out following the methodology described by the manufacturer of the kit. After the expression of the fusion proteins, these were fixed on membrane with gelatine. The membrane was incubated with the specific antiserum for GA enzyme, was neutralized with *E. coli* lysate (contained inside the kit), and then with IgG specifically directed against rabbit antibodies and conjugated with alkaline phosphatase (also contained in the kit).

In the following chromogenic reaction, the positive clone generated blue-violet spots, whilst negative clones and rabbit antiserum used as control did not yield any spots.

The plaque which resulted to be positive was then submitted to in vivo excision protocol (Stratagene lambdaZAPII cloning kit); pWE56.4 plasmid, recovered by means of this methodology, contains, in the lacZ' gene, an internal piece of GA gene of *Pseudomonas* 146H9 (NCIMB40474), and pZAP1.1 plasmid contains that from *Pseudomonas* SY77-1 (Ferm2410). Gene orientation is from $P_{lac}$ ahead.

3. Cloning GA genes from *Pseudomonas* sp. 146H9 and SY77-1 strains.

pWE56.4 plasmid contains an approximately 2.5 kbp long fragment of DNA from *Pseudomonas* 146H9, with at least a portion of DNA coding for GA having formed a fusion protein which positively reacts to the antigenicity test for same enzyme. By definition, this fragment can not contain the full gene coding for GA. A SacII-SalI fragment approximately 1.2 kbp long was isolated from plasmid pWE56.4 and labelled with digoxigenin-dUTP (Boehringer Non-Radioactive Labelling Kit), for use as DNA probe. The same lambdaZAPII *Pseudomonas* 146H9 gene library was assayed in order to identify the presence of plaques containing DNA which ibridizes with this probe. A positive plaque was located among 10000 assayed plaques.

The corresponding plasmids were extracted by following the in vivo excision protocol and *E. coli* cells, transformed with the same plasmid, to which the designation "pWE3.1" was assigned (FIG. 1: Physical map of plasmid pWE3.1. The shaded area contains the GA gene from *Pseudomonas* 146H9 (NCIMB40474). The solid black region belongs to pBluescriptSK+/−plasmid), were assayed for their capability of hydrolizing GL-7ACA into 7ACA. It was found that pWE3 contains a 10 kbp long fragment of *Pseudomonas* sp. 146H9 DNA and is capable of transferring the acylasic activity to *E. coli* (Table 2). On this fragment, no sites were found for EcoRI, HindIII, BamHI, BclI, KpnI, ScaI, HpaI, MluI, PvuI, PvuII, Asp718, DraI, SmaI. The positions of the sites for SacII, PstI, XbaI, EcoRV, BglII are shown in FIG. 1.

pZAP1.1 plasmid bears a 3 kbp long fragment of *Pseudomonas* SY77-1 DNA, containing at least a portion of DNA coding for GA, because it is capable of coding for a fusion protein which positively reacts to the antigenicity test against GA enzyme. By definition, this fragment can not contain the full-length GA gene. From this pZAP1.1 plasmid, a 0.6 kbp EcoRI-PstI fragment was isolated which was labelled with digoxigenin-dUTP (Boehringer Non-Radioactive Labelling Kit), for use as a DNA probe.

With that probe, also the *Pseudomonas* SY77-1 lambdaZAPII gene library was screened, and, from 7000 screened plaques, a plaque was found which is capable of hybridizing to the same probe.

The corresponding plasmids were extracted by following the in vivo excision procedure, and were used to transform *E. coli* cells; those cells which contain said plasmid, named "pWG2" were then tested for their capacity of hydrolizing GL-7ACA into 7ACA.

pWG2 plasmid contains a 3 kbp fragment of *Pseudomonas* sp. SY77-1 DNA, which is capable of transforming *E. coli* into an acylase-positive strain (Table 2).

4. DNA restriction to find the essential region coding for GA.

pWE3.1 plasmid (1μg) was cut with XbaI, and a 7 kbp long fragment was isolated by electroelution, and was then circularized again by T4 DNA ligase. Cells of *E. coli* XL1 Blue were transformed with the same mixture and the resulting plasmid, pWE2.20, was isolated. The deletion of a 6 kbp XbaI fragment from pWE3.1 generated pWE2.20, which displays a similar enzymatic activity (Table 2). Therefore, the gene coding for *Pseudomonas* 146H9 GA must be on a 4 kbp long DNA fragment between EcoRI and XbaI sites.

We consider that the 3 kbp long fragment of pWG2, containing the GA gene from SY77-1, is already restricted enough to be transferred to an expression vector.

5. Cloning the genes coding for GA in a procariotic expression vector.

4 kbp long EcoRI-XbaI fragment of pWE3.1, containing the GA gene from *Pseudomonas* 146H9 was cloned to pKK223-3 (Pharmacia), which uses the hybrid triptophan/lactose promoter ($P_{tac}$) as a strong and inducible expression signal. The EcoRI-XbaI fragment (1 g) was only modified at the XbaI site, with Klenow DNA polymerase (2 U), (partially) filling the site with 0.2 mM dCTP and dTTP in nick-translation buffer (1 hour, room temperature), to have a suitable fragment for cloning in pKK223-3 digested with EcoRI-HindIII.

Figure 2:
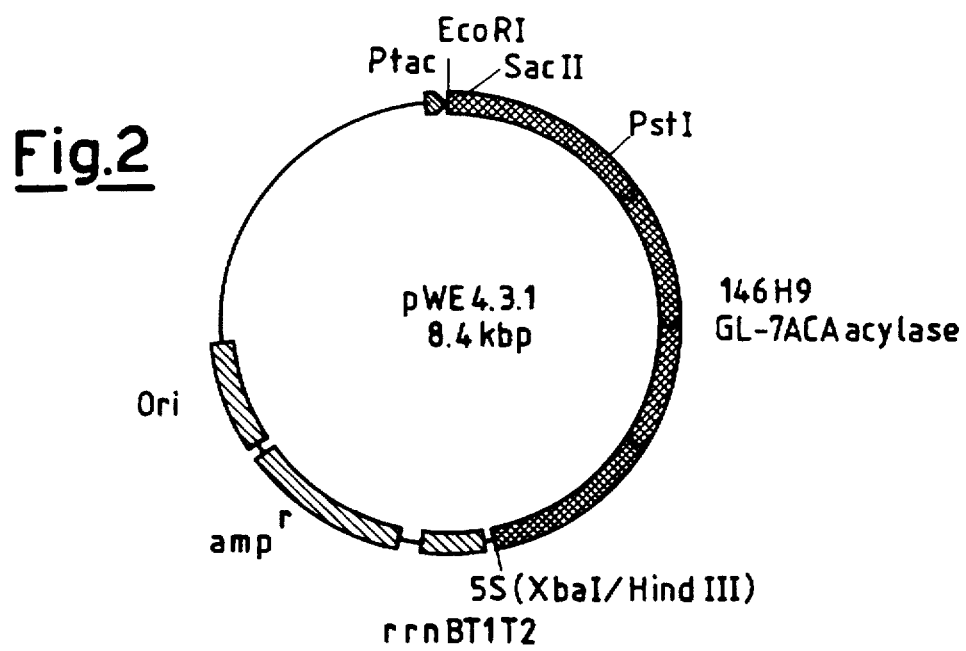
FIG. 2 is a plasmid map of pWE4.3.1.

The resulting pWE4.3.1 plasmide [FIG. 2: physical map of pWE4.3.1 plasmid. The shaded area contains the GA gene from *Pseudomonas* 146H9 (NCIMB40474)] is used to transform *E. coli* XL1 Blue into GA-positive cells; the transformed cells displayed an acylase activity of 60 U/l, which is 30 times as high as the activity found with pWE3.1 and approximately 20 times as high as than of the activity of the original *Pseudomonas* strain.

XL1Blue strain (pWE4.3.1) was deposited with NCIMB and was assigned the Accession No. NCIMB40560.

The 3 kbp long EcoRI fragment of pWG2 plasmid, containing the gene coding for GA enzyme of *Pseudomonas* SY77-1 was cloned into the EcoRI site of pKK223-3 and, using the ligation mixture, was used to transform *E. coli* XL1Blue.

Figure 3:
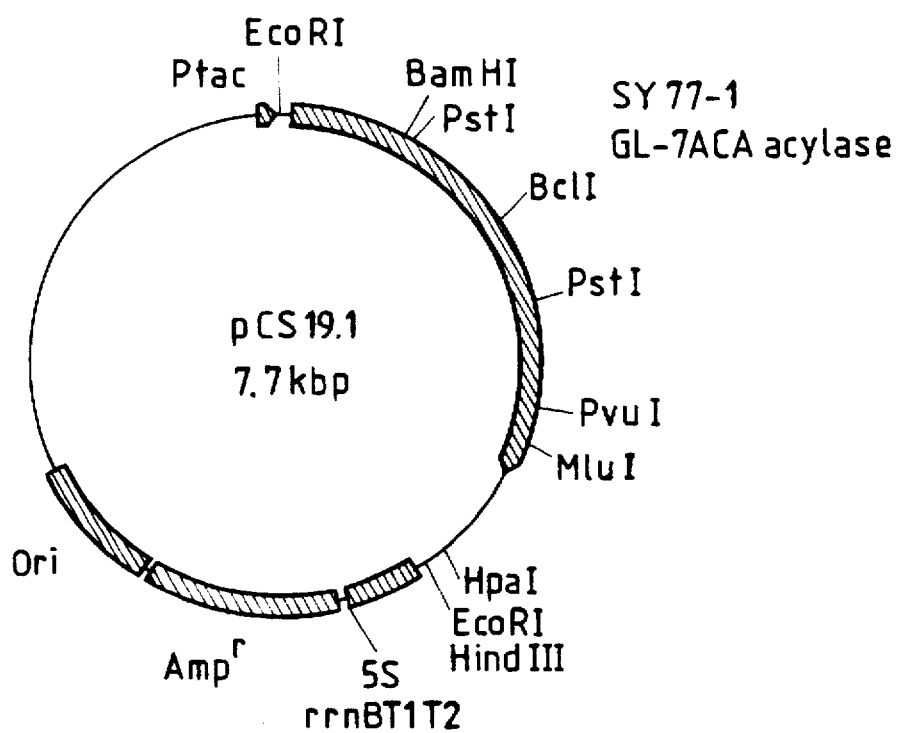
FIG. 3 is a plasmid map of pCS19.1.

From the obtained transormants, the pCS19.1 plasmid was isolated (FIG. 3: Physical map of pCS19.1 plasmid. The GA gene of SY77-1 is in the region indicated by the black arrow.), overproducing GA.

XL1Blue strain (pCS19.1) was deposited with NCIMB and it was assigned the Accession No. NCIMB40559.

pCS19.1 plasmid was also used to transform W3110 (ATCC27325) and DH1. Both these strains have a Lac⁻ genotype.

The pKK223-3 vector was furthermore modified by inserting tetracycline resistance instead of ampicillin resistance and thus eliminating the β-lactamases deriving from that plasmid. For that purpose, from pBR322 plasmid the AvaI-HindIII DNA fragment approximately of 1.4 Kb was isolated, which contains the gene for tetracycline resistance. This DNA fragment was treated with Klenow DNA polimerase enzyme, so as to produce blunt terminal ends. On the contrary, pKK223-3 vector was cut at the ScaI site contained in the gene for ampicillin resistance, and was then dephosphorylated.

Figure 4:
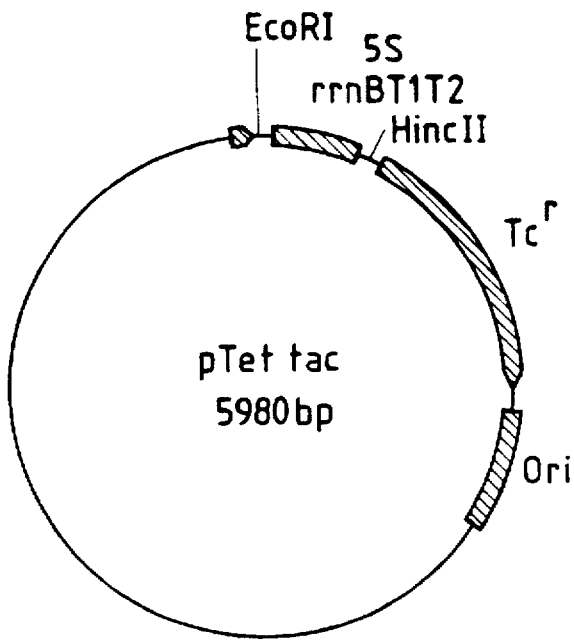
FIG. 4 is a plasmid map of pTet tac.

The so obtained fragment and vector were ligated with T4 DNA ligase at 16° C. overnight, and the resulting ligation mixture was used in order to transform E. coli JM105. Those colonies which displays resistance to tetracycline (50 μg/ml) contain the pTet tac plasmid (FIG. 4).

Figure 5:
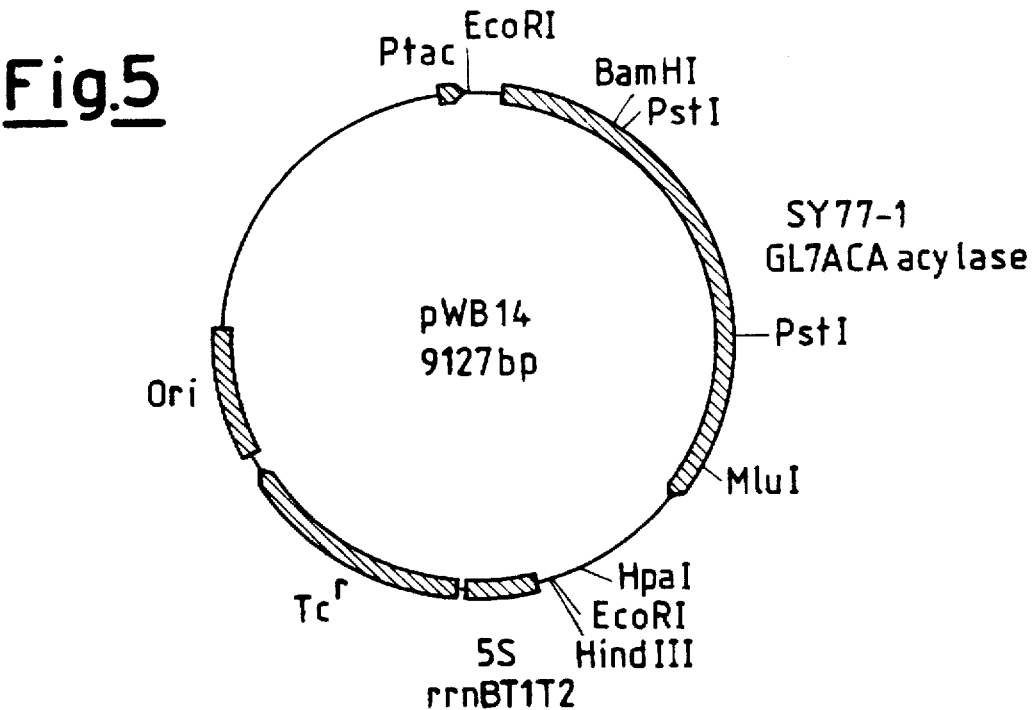
FIG. 5 is a plasmid map of pWB14.
Figure 6:
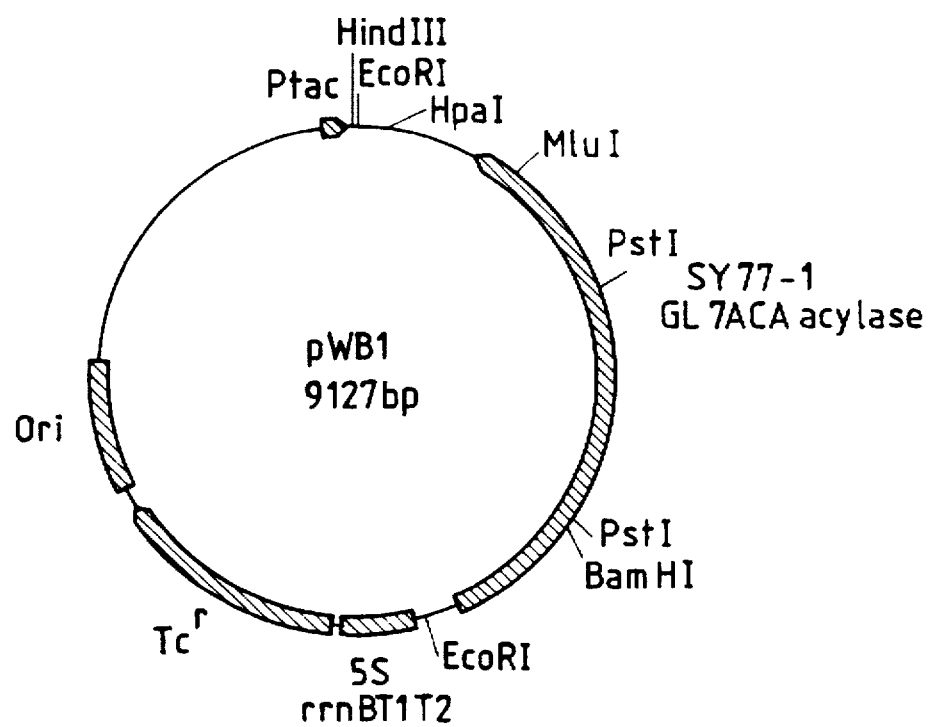
FIG. 6 is a plasmid map of pWB1.

This plasmid was then isolated (10 μg) and incubated for 1 hour at 37° C. with 100 U of EcoRI enzyme and was then dephosphorylated; furthermore, from pWG2 plasmid, by the EcoRI enzyme, the 3 Kb fragment containing the GA gene from SY77-1 was cut out. The resulting linearized vector and fragment were then ligated with T4 DNA ligase. In that way, the pWB14 plasmid was obtained (FIG. 5), in that case when GA gene is oriented in the same direction as of $P_{tac}$ promoter, and pWB1 plasmid (FIG. 6) in that case when the GA gene is oriented in the opposite direction to $P_{tac}$ promoter (in that way, the expression thereof is independent from $P_{tac}$).

Both pWB14 and pWB1 plasmids make it possible GA enzyme to be obtained, as also pCS19.1, but without obtaining the β-lactamases, replaced by resistance to tetracycline; furthermore, in pWB1, GA enzyme does not result to be under control by $P_{tac}$ promoter.

bacto-tryptone 0.4%, NaCl 0.4%, tetracycline 10 μg/ml, ampicillin 50 μg/ml).

A loop of strain stored on YT-glycerol medium was streaked on a Petri plate with LB Agar (composition: bacto-yeast extract 0.5%, bacto-tryptone 1%, NaCl 1%, Agar 1.5%, tetracycline 10 μg/ml, ampicillin 50 μg/ml), and the plate was incubated at 37° C. overnight.

A sterile tube containing 2 ml of LB+Tc+Ap medium (composition: bacto-yeast extract 0.5%, bacto-tryptone 1%, NaCl 1%, tetracycline 10 μg/ml, ampicillin 50 μg/ml) was inoculated with a single colony from LB Agar plate, and was incubated at 30° C. for 16 hours, shaken at 200 rpm.

An ErLenmeyer flask of 500 ml of capacity containing 100 ml of LB+Tc+Ap+IPTG broth (composition: bacto-yeast extract 0.5%, bacto-tryptone 1%, NaCl 1%, tetracycline 10 μg/ml, ampicillin 50 μg/ml, IPTG 1 mM) was inoculated with 100 μl of LB culture, was incubated for 24 hours at 30° C. and shaken at 300 rpm. The OD550 (optical density at 550 nm) of the culture was 6.0.

The cells were then centrifuged at 5000 rpm for 10 minutes and were then resuspended, in the same volume as the original volume, of Tris.Cl 0.1M NaCl 0.05M ph 8.0. The cells were then broken by sonication, and the activity of GA enzyme in the cellular extract was evaluated by a colorimetric technique.

The activity of GA was 60 U/l, which is 20 times as high as of the original strain Pseudomonas sp. 1 46H9.

EXAMPLE 3

This example relates to the fermentation of E. coli XL1Blue (pWE4.3.1) in a new fermentation broth for GA enzyme production.

TABLE 2

Acylasic activity of strains mentioned in the patent

| Strain | Plasmid | Broth | Activity U/l | Specific activity of total proteins, U/g |
|---|---|---|---|---|
|  |  | NB | 3 | 4 |
| E. coli XL1-Blue | pWE3.1 | LB/Tc + Ap | 2 | 4 |
| E. coli XL1-Blue | pWE2.20 | LB/Tc + Ap | 3 | 5 |
| E. coli XL1-Blue | pWE4.3.1 | LB/Tc + Ap | 10 | 23 |
| E. coli XL1-Blue | pWE4.3.1 | LB/Tc + Ap + IPTG | 60 | 134 |
| E. coli XL1-Blue | pWE4.3.1 | CSL/Tc + Ap | 55 | 121 |
| E. coli XL1-Blue | pWE4.3.1 | CSL/fedbatch + glucose | 6000 | 125 |
| Pseudomonas SY77-1 |  | NB | 4 | 5 |
| E. coli XL1-Blue | pWG2 | LB/Tc + Ap | 3 | 6 |
| E. coli XL1-Blue | pCS19.1 | LB/Tc + Ap | 22 | 48 |
| E. coli XL1-Blue | pCS19.1 | LB/Tc + Ap + IPTG | 140 | 279 |
| E. coli W3110 | pCS19.1 | LB/Tc + Ap | 136 | 269 |
| E. coli DHI | pCS19.1 | LB/Tc + Ap | 135 | 284 |
| E. coli XL1-Blue- | pCS19.1 | CSL/Tc + Ap | 307 | 410 |
| E. coli XL1-Blue | pCS19.1 | CSL/fedbatch + glucose | 9780 | 849 |
| E. coli JM 105 | pWB14 | LB/Sm + Tc + IPTG | 135 | 250 |
| E. coli JM 105 | pWB14 | CSL/Sm + Tc | 330 | 355 |
| E. coli JM 105 | pWB1 | LB/Sm + Tc | 140 | 100 |
|  |  | LB/Sm + Tc + IPTG | 130 | 195 |
|  |  | CSL/Sm + Tc | 787 | 280 |

EXAMPLE 2

This example relates to the production of GA enzyme of E. coli XL1Blue (pWE4.3.1) strain, obtained as disclosed in Example 1.

The strain is stored at −40° C. in YT glycerol medium (composition: glycerol 15%, bacto-yeast extract 0.7%, The inoculum was prepared as disclosed in Example 2.

An Erlenmeyer flask of 500 ml of capacity containing 100 ml od CSL broth (composition: Corn-Steep Liquor ex Societ á Piemontese Amido Derivati 14%, tetracycline 10 μg/ml, ampicillin 50 μg/ml, pH 7.5) was inoculated with 100 μl of LB culture and was then incubated for 24 hours at 30° C., under shaking at 300 rpm. The OD550 of the culture was 6.5.

The cells were spun at 5000 rpm for 10 minutes and were then resuspended, in the same volume as the original volume, of Tris.Cl 0.1M NaCl 0.05M pH 8.0. The cells were broken by sonication and the activity of GA enzyme in the cellular extract was titrated by the colorimetric method.

An activity of 55 U/l was found, which is about 18 times as high as of the original *Pseudomonas* sp. 146H9 strain.

EXAMPLE 4

This example relates to a new type of fermentation of *E. coli* XL1Blue (pWE4.3.1) for GA enzyme production.

The inoculum was prepared as disclosed in Example 2.

An Erlenmeyer flask of 500 ml with 100 ml of LB+Tc+Ap broth (composition: bacto-yeast extract 0.5%, bacto-tryptone 1%, NaCl 1%, tetracycline 10 µg/ml, ampicillin 50 µg/ml) was inoculated with 100 µl of LB culture and was incubated at 30° C. and 300 rpm for 24 hours. The OD550 of the culture was 6.0.

A fermentor (2 l, INFORS HG) containing 1.5 l of CSL (composition: Corn-Steep Liquor 14%, pH 7.5) was inoculated with 100 ml of LB culture. The fermentation parameters were: T 30° C., stirring 1300 rpm, air flow rate 1 vvm during 20 hours until OD550=6.0. During the following 10 hours, to the culture a glucose or glycerol solution (50% W/v) was added as a continuous stream with a flow rate which was first of 1.5 ml/l.h and then of 6 ml/l.h, during approximately 15 hours, with pH being kept at 7.5 (with NaOH 5M), and with such a dissolved oxygen level, as to have $PO_2$=10%. The end growth observed was OD550=90. At the end of the culture, the cumulated biomass was of 89 g/l (dry weight 18 g/l). pWE4.3.1 plasmid was still present in 70% of cells after a 54-hour fermentation at maximal production.

The cells were centrifuged at 5000 rpm for 10 minutes and were subsequently resuspended, in the same volume as the original volume, of Tris.Cl 0.1M NaCl 0.05M pH 8.0. The cells were broken by sonication and in the cellular extract the activity of GA was titrated by colorimetry. A GA activity of 6000 U/l was found, which is 2000 times as high as of the original *Pseudomonas* 146H9 strain.

EXAMPLE 5

This example relates to the production of GA enzyme of *E. coli* XL1Blue (pCS19.1) obtained as disclosed in Example 1.

The inoculum was prepared as disclosed in Example 2.

An Erlenmeyer flask of 500 ml containing 100 ml of LB+Tc+Ap+IPTG broth (composition: bacto-yeast extract 0.5%, bacto-tryptone 1%, NaCl 1%, tetracycline 10 µg/ml, ampicillin 50 µg/ml, IPTG 1 mM) was inoculated with 100 µl of LB culture and was incubated at 30° C. and 300 rpm for 24 hours. The OD550 of the culture was 6.0.

The cells were centrifuged at 5000 rpm for 10 minutes and were subsequently resuspended, in the same volume as the original volume, of Tris.Cl 0.1M NaCl 0.05M pH 8.0. The cells were broken by sonication and in the cellular extract the activity of GA was titrated by colorimetry. A GA activity of 140 U/l was found, which is 35 times as high as of the original *Pseudomonas* sp. SY77-1 strain.

EXAMPLE 6

This example relates to the production of GA enzyme from *E. coli* W3110 strain, transformed with pCS19.1.

The strain is stored at –40° C. in YT glycerol medium (composition: glycerol 15%, bacto-yeast extract 0.7%, bacto-tryptone 0.4%, NaCl 0.4%, ampicillin 50 µg/ml).

The strain grown on YT-glycerol broth, was seeded with a loop on a Petri plate with LB Agar+Ap (composition: bacto-yeast extract 0.5%, bacto-tryptone 1%, NaCl 1%, Agar 1.5%, ampicillin 50 µg/ml), and the plate was incubated at 37° C. overnight.

A sterile tube containing 2 ml of LB+Ap medium (composition: bacto-yeast extract 0.5%, bacto-tryptone 1%, NaCl 1%, ampicillin 50 µg/ml) was inoculated with a single colony from LB Agar plate, and was incubated at 30° C. for 16 hours, shaken at 200 rpm.

An Erlenmeyer flask of 500 ml of capacity containing 100 ml of LB+Ap broth (composition: bacto-yeast extract 0.5%, bacto-tryptone 1%, NaCl 1%, ampicillin 50 µg/ml) was inoculated with 100 µl of LB culture, was incubated for 24 hours at 30° C. and shaken at 300 rpm. The OD550 (optical density at 550 nm) of the culture was 6.0.

The cells were then centrifuged at 5000 rpm for 10 minutes and were subsequently resuspended, in the same volume as the original volume, of Tris.Cl 0.1M NaCl 0.05M pH 8.0. The cells were then broken by sonication, and the activity of GA enzyme in the cellular extract was titrated by a colorimetric technique.

The activity of GA resulted to be of 136 U/l, which is 34 times as high as of the original strain *Pseudomonas* SY77-1.

EXAMPLE 7

This example relates to the production of GA enzyme from *E. coli* DHI strain, transformed with pCS19.1.

The inoculum was prepared as disclosed in Example 6.

A sterile tube containing 2 ml of LB+Ap medium (composition: bacto-yeast extract 0.5%, bacto-tryptone 1%, NaCl 1%, ampicillin 50 µg/ml) was inoculated with a single colony from LB Agar plate, and was incubated at 30° C. for 16 hours, shaken at 200 rpm.

An Erlenmeyer flask of 500 ml of capacity containing 100 ml of LB+Ap broth (composition: bacto-yeast extract 0.5%, bacto-tryptone 1%, NaCl 1%, ampicillin 50 µg/ml) was inoculated with 100 µl of LB culture, was incubated for 24 hours at 30° C. and shaken at 300 rpm. The OD550 (optical density at 550 nm) of the culture was 6.0.

The cells were then centrifuged at 5000 rpm for 10 minutes and were subsequently resuspended, in the same volume as the original volume, of Tris.Cl 0.1M NaCl 0.05M pH 8.0. The cells were then broken by sonication, and the activity of GA enzyme in the cellular extract was titrated by a colorimetric technique.

The activity of GA resulted to be of 135 U/l, which is 34 times as high as of the original strain *Pseudomonas* SY77-1.

EXAMPLE 8

This example relates to the fermentation of *E. coli* XL1Blue (pCS19.1) in a new fermentation broth for GA enzyme production.

The inoculum was prepared as disclosed in Example 2.

An Erlenmeyer flask of 500 ml of capacity containing 100 ml of CSL broth (composition: Corn-Steep Liquor ex Societ à Piemontese Amido Derivati 14%, tetracycline 10 µg/ml, ampicillin 50 µg/ml, pH 7.5) was inoculated with 100 µl of LB culture and was then incubated for 24 hours at 30° C., under shaking at 300 rpm. The OD550 of the culture was 6.7.

The cells were spun at 5000 rpm for 10 minutes and were then resuspended, in the same volume as the original volume, of Tris.Cl 1M NaCl 0.05M pH 8.0. The cells were broken by sonication and the activity of GA enzyme in the cellular extract was titrated by the colorimetric method.

An activity of 307 U/l was found, which is about 77 times as large as of the original *Pseudomonas* sp. SY77-1.

EXAMPLE 9

This example relates to a new type of fermentation of *E. coli* XL1Blue (pCS19.1) for GA enzyme production.

The inoculum was prepared as disclosed in Example 2.

An Erlenmeyer flask of 500 ml containing 100 ml of LB+Tc+Ap broth (composition: bacto-yeast extract 0.5%, bacto-tryptone 1%, NaCl 1%, tetracycline 10 µg/ml, ampicillin 50 µg/ml) was inoculated with 100 µl of LB culture and was incubated at 30° C. and 300 rpm for 24 hours. The OD550 of the culture was 6.0.

A fermentor (2 l, INFORS HG) containing 1.5 l of CSL (composition: Corn-Steep Liquor 14%, pH 7.5) was inoculated with 100 ml of LB culture. The fermentation parameters were: T 30° C., stirring 1300 rpm, air flow rate 1 vvm during 20 hours until OD550=6.0. During the following 10 hours, to the culture a glucose or glycerol solution (50% W/v) was added as a continuous stream, at a flow rate which was first of 1.5 ml/l.h and then of 6 ml/l.h, during approximately 16 hours, with pH being kept at 7.5 (with NaOH 5M), and with such a dissolved oxygen level, as to have $PO_2$=10%. The end growth observed was OD550=90. At the end of the culture, the cumulated biomass was of 87 g/l (dry weight 18 g/l) .

pCS19.1 plasmid was still present in 84% of cells after a 54-hour fermentation, i.e., the needed time for maximal production.

The cells were centrifuged at 5000 rpm for 10 minutes and were subsequently resuspended, in the same volume as the original volume, of Tris.Cl 0.1M NaCl 0.05M pH 8.0. The cells were broken by sonication and in the cellular extract the activity of GA was titrated by colorimetry. The GA activity was of 9780 U/l.

A GA activity of 9780 U/l was found, which is 2445 times as high as of the original *Pseudomonas* sp. SY77-1 strain.

EXAMPLE 10

This example relates to the production of GA enzyme from *E. coli* JM 105 (pWB14) strain, obtained as disclosed in Example 1.

The strain is stored at −40° C. in YT glycerol medium (composition: glycerol 15%, bacto-yeast extract 0.7%, bacto-tryptone 0.4%, NaCl 0.4%, tetracycline 25 µg/ml, streptomycin 125 µg/ml).

A loop of strain stored on YT-glycerol medium was streaked on a Petri plate with LB Agar (composition: bacto-yeast extract 0.5%, bacto-tryptone 1%, NaCl 1%, tetracycline 25 µg/ml, streptomycin 125 µg/ml), and the plate was incubated at 37° C. overnight.

A sterile tube containing 2 ml of LB+Sm+Tc medium (composition: bacto-yeast extract 0.5%, bacto-tryptone 1%, NaCl 1%, tetracycline 25 µg/ml, streptomycin 125 µg/ml) was inoculated with a single colony from LB Agar plate, and was incubated at 30° C. for 16 hours, shaken at 200 rpm.

An Erlenmeyer flask of 500 ml of capacity containing 100 ml of LB+Tc+Sm+IPTG broth (composition: bacto-yeast extract 0.5%, bacto-tryptone 1%, NaCl 1%, tetracycline 25 µg/ml, streptomycin 125 µg/ml, IPTG 1 mM) was inoculated with 100 µl of LB culture, was incubated for 24 hours at 30° C. and shaken at 300 rpm. The OD550 (optical density at 550 nm) of the culture was 5.0.

The cells were then centrifuged at 5000 rpm for 10 minutes and were subsequently resuspended, in the same volume as the original volume, of Tris.Cl 0.1M NaCl 0.05M pH 8.0. The cells were then broken by sonication, and the activity of GA enzyme in the cellular extract was evaluated by a colorimetric technique.

The activity of GA resulted to be of 135 U/l, which is 34 times as high as of the original strain *Pseudomonas* sp. SY77-1.

EXAMPLE 11

This example relates to the fermentation of *E. coli* JM105 (pWB14) in a new fermentation broth for GA enzyme production.

An inoculum was prepared as disclosed in Example 10.

An Erlenmeyer flask of 500 ml of capacity containing 100 ml of CSL broth (composition: Corn-Steep Liquor ex Societ á Piemontese Amido Derivati 14%, tetracycline 25 µg/ml, streptomycin 125 µg/ml, pH 7.5) was inoculated with 100 µl of LB culture and was then incubated for 24 hours at 30° C., under shaking at 300 rpm. The OD550 of the culture was 8.

The cells were spun at 5000 rpm for 10 minutes and were then resuspended, in the same volume as the original volume, of Tris.Cl 0.1M NaCl 0.05M pH 8.0. The cells were broken by sonication and the activity of GA enzyme in the cellular extract was titrated by the colorimetric method.

A GA activity of 330 U/l was found, which is 83 times as large as of the original *Pseudomonas* sp. SY77-1 strain.

EXAMPLE 12

This example relates to the production of GA enzyme from *E. coli* JM105 (pWB1) strain, obtained as disclosed in Example 1.

The strain is stored at −40° C. in YT glycerol medium (composition: glycerol 15%, bacto-yeast extract 0.7%, bacto-tryptone 0.4%, NaCl 0.4%, tetracycline 25 µg/ml, streptomycin 125 µg/ml.

A loop of strain stored on YT-glycerol medium was streaked on a Petri plate with LB Agar (composition: bacto-yeast extract 0.5%, bacto-tryptone 1%, NaCl 1%, tetracycline 25 µg/ml, streptomycin 125 µg/ml), and the plate was incubated at 37° C. overnight.

A sterile tube containing 2 ml of LB+Sm+Tc medium (composition: bacto-yeast extract 0.5%, bacto-tryptone 1%, NaCl 1%, tetracycline 25 µg/ml, streptomycin 125 µg/ml) was inoculated with a single colony from LB Agar plate, and was incubated at 30° C. for 15 hours, shaken at 200 rpm.

An Erlenmeyer flask of 500 ml of capacity containing 100 ml of LB+Tc+Sm broth (composition: bacto-yeast extract 0.5%, bacto-tryptone 1%, NaCl 1%, tetracycline 25 µg/ml, streptomycin 125 µg/ml) was inoculated with 100 µl of LB culture, was incubated for 24 hours at 30° C. and shaken at 300 rpm. The OD550 (optical density at 550 nm) of the culture was 5.

The cells were then centrifuged at 5000 rpm for 10 minutes and were subsequently resuspended, in the same volume as the original volume, of Tris.Cl 0.1M NaCl 0.05M pH 8.0. The cells were then broken by sonication, and the activity of GA enzyme in the cellular extract was evaluated by a colorimetric technique.

The activity of GA resulted to be of 140, which is 35 times as high as of the original strain *Pseudomonas* sp. SY77-1.

EXAMPLE 13

This example relates to the production of GA enzyme from *E. coli* JM195 (pWB1) obtained as disclosed in Example 1.

The inoculum was prepared as disclosed in Example 12.

An Erlenmeyer flask of 500 ml of capacity containing 100 ml of LB+Tc+Sm+IPTG broth (composition: bacto-yeast extract 0.5%, bacto-tryptone 1%, NaCl 1%, tetracycline 25 µg/ml, streptomycin 125 µg/ml, IPTG 1 mM) was inoculated with 100 µl of LB culture and was then incubated for 24 hours at 30° C., under shaking at 300 rpm. The OD550 of the culture was 5.

The cells were spun at 5000 rpm for 10 minutes and were then resuspended, in the same volume as the original volume, of Tris.Cl 0.1M NaCl 0.05M pH 8.0. The cells were broken by sonication and the activity of GA enzyme in the cellular extract was titrated by the colorimetric method.

A GA activity of 130 was found, which is 33 times as high as of the original *Pseudomonas* sp. SY77-1 strain.

EXAMPLE 14

This example relates to the fermentation of *E. coli* JM105 (pWB1) in a new fermentation broth for GA enzyme production.

The inoculum was prepared as disclosed in Example 12.

An Erlenmeyer flask of 500 ml of capacity containing 100 ml of CSL broth (composition: Corn-Steep Liquor ex Societ á Piemontese Amido Derivati 14%, tetracycline 25 µg/ml, streptomicyn 125 µg/ml, pH 7.5) was inoculated with 100 µl of LB culture and was then incubated for 24 hours at 30° C., under shaking at 300 rpm. The OD550 of the culture was 8.5.

The cells were spun at 5000 rpm for 10 minutes and were then resuspended, in the same volume as the original volume of Tris.Cl 0.1M NaCl 0.05M pH 8.0. The cells were broken by sonication and the activity of GA enzyme in the cellular extract was titrated by the colorimetric method.

A GA activity of 78 U/l was found, which is 197 times as high as of the original *Pseudomonas* sp. SY77-1 strain.

What is claim as new and desired to be secured by Letters Patent of the United States is:

1. The *E. coli* strain XL1Blue/pWE4.3.1 deposited under accession number NCIMB40560.
2. The plasmid pWE4.3.1 which is maintained in the strain of claim 1.
3. The *E. coli* strain XL1Blue pCS19.1 deposited under accession number NCIMB40559.
4. The plasmid pCS19.1 which is maintained in the *E. coli* strain of claim 3.
5. The *E. coli* strain JM105/pWB14 deposited under accession number NCIMB40593.
6. The plasmid pWB14 which is maintained in the *E. coli* strain of claim 5.

* * * * *